United States Patent [19]

Bertolacini et al.

[11] 4,062,802
[45] Dec. 13, 1977

[54] CARBON MONOXIDE TREATMENT OF A PHOSPHORUS-VANADIUM-ZINC OXYGEN CATALYST

[75] Inventors: Ralph J. Bertolacini, Chesterton, Ind.; Robert M. Koca, Glen Ellyn, Ill.

[73] Assignee: Standard Oil Company (Indiana), Chicago, Ill.

[21] Appl. No.: 685,716

[22] Filed: May 12, 1976

[51] Int. Cl.$^2$ .................... B01J 27/14; C07D 307/60
[52] U.S. Cl. ................................... 252/435; 252/437; 260/346.74
[58] Field of Search .............................. 252/437, 435

[56] References Cited

U.S. PATENT DOCUMENTS

| | | | |
|---|---|---|---|
| 3,156,705 | 11/1964 | Kerr | 252/437 X |
| 3,288,721 | 11/1966 | Kerr | 252/437 X |
| 3,293,268 | 12/1966 | Bergman et al. | 252/437 X |
| 3,888,886 | 6/1975 | Young et al. | 252/437 X |
| 3,907,833 | 9/1975 | Slinkard et al. | 252/437 X |

*Primary Examiner*—Patrick P. Garvin
*Assistant Examiner*—William G. Wright

*Attorney, Agent, or Firm*—Robert E. Sloat; Arthur G. Gilkes; William T. McClain

[57] ABSTRACT

A catalytic composition is produced by reacting in an aqueous medium, vanadium and phosphorus compounds together with a hydrogen halide and removing liquid from the resulting reactants to form a solid which in an improved manner is heated at a temperature of about less than 470° C. to effect liberation of water of hydration from the solid and thereafter contacting with a reducing material selected from the group of carbon monoxide, hydrogen and hydrogen sulfide at a temperature of from about 300° to about 600° C. and in the substantial absence of gaseous oxygen other than that liberated from the solid. The specific reduction step as taught and claimed herein improves catalyst activity performance by increasing the catalyst conversion and selectivity to a desired oxygenated product, and the ultimate yield of the oxygenated product per quantity of feed component converted. It also minimizes formation of inactive $VPO_5$, improves the strength of pellets and reduces the residual chloride content of the catalyst.

20 Claims, No Drawings

CARBON MONOXIDE TREATMENT OF A PHOSPHORUS-VANADIUM-ZINC OXYGEN CATALYST

BACKGROUND OF THE INVENTION

1. Field of the Invention

The field of art to which this invention pertains is oxidation catalysts of phosphorus-vanadium-oxygen materials, the method of manufacturing such catalysts and the process use of those materials.

In a specified instance the catalyst contains a metal activator in addition to the phosphorus and vanadium oxygen complex generally selected from the group consisting of zinc, lithium, copper, bismuth, or mixtures thereof.

2. Description of the Prior Art

U.S. Pat. No. 3,293,268 patented Dec. 20, 1966, which relates to a process for the production of maleic anhydride by oxidation of normal butane using a phosphorus-vanadium-oxygen complex catalyst produced in a specified manner.

U.S. Pat. No. 3,862,146, issued Jan. 21, 1975, relates to a process for the oxidation of butane to maleic anhydride using a phosphorus-vanadium-oxygen complex catalyst having a certain atomic ratio of phosphorus to vanadium and additionally containing the metal activator selected from the group consisting of zinc, copper, bismuth, lithium, or mixtures thereof, the metal activators also being present in a certain atomic ratio with respect to vanadium.

Belgian Pat. No. 806,475, issued Apr. 24, 1974, relates to a method of restoring the activity of a phosphorus-vanadium-oxygen metal activated catalyst which has been deactivated by the oxidation of normal butane to maleic anhydride, comprising contacting a deactivated catalyst with a reducing gas such as hydrogen, carbon monoxide, methane, hydrogen sulfide, or mixtures thereof, at a temperature of 400°-600° C. to reduce the vanadium from the +5 to the +4 state thereby reactivating the catalyst for a subsequent process use. The specified teachings of this patent are confined to a reactivation procedure.

U.S. Pat. No. 3,915,892, issued Oct. 28, 1975, relates to a method for the production of vanadium-phosphorus mixed oxide oxidation catalyst incorporating a very specified calcination procedure for producing a catalyst. More specifically in this patent, phase changes characterized as a dihydrate to monohydrate conversion, a monohydrate to anhydrous oxide conversion, and a post-dehydration change occur under specified procedures to effect the production of a catalyst used for the production of maleic anhydride from butane. These three bulk phase transitions as taught in the patent require that oxygen contact the catalyst during all three transitional stages. As illustrated in the examples present in this patent, a method which did not have oxygen present in a final pretreatment step produced an inferior catalyst.

Other relevant prior art may be found in the reference cited against the above-described patents and in other references present in Class 260, sub-class 346.8 and/or Class 252, sub-class 435 and 437.

DETAILED DESCRIPTION OF THE INVENTION

An embodiment of this invention resides in an improved phosphorus-vanadium-oxygen containing complex catalyst having an atomic ratio of phosphorus to vanadium in the range of from about 0.5–5 to 1 produced by a process comprising:

A. reacting a mixture comprising vanadium oxide, pentavalent phosphorus and hydrogen halide in an aqueous solution;

B. Removing liquid from the mixture to form a solid; the improvement comprising;
  1. heating the solid to a temperature of less than about 470° C. to effect liberation of water of hydration;
  2. contacting solid from step 1 with a reducing material comprising a gas selected from the group consisting of CO, $H_2$ and $H_2S$ and mixtures thereof at a temperature of from about 300° to about 600° C. and in the absence of added gaseous oxygen.

In another embodiment, the present invention relates to the improvement in a method for production of a catalyst comprising a phosphorus-vanadium-oxygen complex having an atomic ratio of phosphorus to vanadium in the range of about 0.5–5 to 1 wherein said catalyst is produced by:

A. reacting a mixture comprising vanadium oxide, pentavalent phosphorus and hydrogen halide in an aqueous solution;

B. removing liquid from the mixture to form a solid; the improvement comprising
  1. heating the solid to a temperature of less than about 470° C. to remove water of hydration;
  2. contacting solid from step (1) with a reducing material comprising a gas selected from the group consisting of CO, $H_2$ and $H_2S$ or mixtures thereof at a temperature of from about 300° to about 600° C. and in the absence of added gaseous oxygen.

A further embodiment of our invention resides in a method for production of oxygenated derivatives of lower aliphatics which comprises reacting said lower aliphatics and molecular oxygen in a reaction zone at a temperature of from about 300° to about 600° C. in contact with a catalyst comprising a phosphorus-vanadium-oxygen complex having an atomic ratio of phosphorus to vanadium in the range of about 0.5–5 to 1; wherein the catalyst is produced by:

A. reacting a mixture comprising vanadium oxide, pentavalent phosphorus compound, and hydrogen halide in an aqueous solution;

B. removing liquid from the mixture to form a solid; wherein an improvement which comprises:
  1. heating the solid to a temperature of about 470° C. to effect removal of water of hydration;
  2. contacting solid from step (1) with a reducing material comprising a gas selected from the group consisting of CO, $H_2$, $H_2S$, and mixtures thereof at a temperature of from about 300° to about 600° C. and in the absence of added gaseous oxygen.

In a preferred embodiment, step (1) of the improvement described above is performed by heating the solid in the presence of an inert gas in the essential absence of gaseous oxygen other than that liberated from the solid to a temperature of less than about 470° C. to effect liberation of water of hydration. Additionally, as another preferred embodiment, the phosphorus-vanadium-oxygen containing complex catalyst contains a metal activator selected from the group consisting of zinc, copper, lithium copper, bismuth, or mixtures thereof, and in an atomic ratio of the metal activator to vanadium in the range of from about 0.05-0.5 to 1.

These and other embodiments and objects of the invention will be more clearly defined in the remaining specification.

The improved composition of matter, the process using it, or the process for manufacturing it, relate to phosphorus-vanadium-oxygen complex catalysts which contain an atomic ratio of phosphorus to vanadium in the range of from about 0.5-5 to 1. In a preferred instance the catalyst contains a metal activator present in an atomic ratio of metal activator to vanadium in the range of from about 0.05-5 to 1. The metal activator is generally selected from the group consisting of zinc, copper, bismuth, lithium, or mixtures thereof. Other metal activators may be incorporated as active components in the catalytic composition of matter, the process using it or the method of manufacturing such catalyst.

The general composition of matter is described, except for the inventive nature of the improved method of manufacturing it in U.S. Pat. No. 3,862,146, issued Jan. 21, 1965, on application Ser. No. 301,613, filed Oct. 27, 1972, having as an inventor E. M. Boghosian. All the teachings of this patent are incorporated into this specification by reference herein.

As described in the above referenced patent, the catalyst can be prepared by mixing vanadium oxide, preferably vanadium pentoxide, together with phosphoric acid and an aqueous solution of a hydrogen halide such as hydrogen chloride. The mixture is allowed to react forming the phosphorus-vanadium-oxygen complex. In some instances they may be heated to increase the rate of reaction and formation of the complex. In other instances it may be desirable to add a metallic activator as described above such as a zinc, copper, lithium, or bismuth compound or mixtures thereof. Other activator materials can be added to the mixture or to the finished catalyst. In the instance in which zinc is used as an activator it can be added as zinc chloride or as metallic zinc at most any stage of the preparation.

After the reaction of the above to produce a liquid mixture the hydrochloric acid and water can be distilled off at around a temperature of 90°-150° C. to form a thick syrup. This distillation step can occur under an ambient atmosphere and in some instances may be performed under vacuum.

The syrup can then be dried to a cake generally in the presence of air and in many instances under atmospheric conditions, at a temperature of around 110°-200° C., a temperature of around 140° C. being preferred to prevent unnecessary oxidation reaction of the material prior to the specified and improved pretreatment procedure claimed herein. After a dry cake has been formed at the above temperatures it can be ground to a suitable particle size, combined with a binder, pelletized and thereafter calcined under controlled conditions to prevent unnecessary temperature runaways of the catalyst particles. Alternately, for fluid bed catalysts, the solid can be ground to a fine particle size for proper fluidizing properties.

The pelletized material is then heated to effect the liberation of water of hydration forming an essentially unhydrated complex. The contact temperature for this procedure is generally less than about 470° C. and preferably less than about 440° C. to prevent the unnecessary oxidation and/or reaction of the complex which would adversely affect its performance and subsequent use. In this step, the particular physical method used to liberate the water of hydration from the solid material determines whether oxygen containing or inert gas blankets contact the solid. In a continuous calcination procedure such as in a zoned belt calcinator, the catalyst particles can be dried in varying stages up to a maximum temperature of around 440° C. without regard to over-oxidizing or damaging the catalyst performance properties. The oxidation of binder material can be regulated more easily in this type of calcination procedure.

In instances in which large beds of particles containing binder material are to be calcined in enclosed vessels, it is essential that a very controlled calcination take place. Preferably the solid should be heated, in the presence of an inert gas and most preferably in the essential absence of gaseous oxygen added to the inert gas, to a temperature of less than about 470° C. to effect liberation of water hydration. By essentially eliminating added gaseous oxygen in this procedure a catalyst suitable for the second stage pretreatment step claimed herein can be produced. In some instances minor quantities of oxygen liberated from the solid itself may be present in the effluent from this step.

In a specified instance, the first drying step on the solid should take place at a maximum temperature of from about 370°-440° C. with a purge of 100% nitrogen gas eliminating oxygen from contacting the catalyst during this procedure except for any oxygen liberated from the catalyst. This step can be performed anywhere from a period of minutes to hours so as to essentially eliminate volatile materials including the liberation of water of hydration and preferably should take place until a constant weight material is produced. This presumably would effectuate the removal of all water of hydration possibly with the altering of the crystalline structure of this material during this step.

In the next step of the two-step treatment improvement the catalyst is contacted with a reducing material which comprises a gas selected from the group consisting of carbon monoxide, hydrogen, and hydrogen sulfide, or mixtures thereof, at a temperature of from about 300° to about 600° C. and in the essential absence of added gaseous oxygen other than that liberated from the solid. The preferable range of temperature contact using the reducing gas is from about 300°-600° C. and more preferably, in a range of from about 400° to about 500° C. An even more specific and preferred range of temperatures are those anywhere from about 425° to about 480° C.

The reducing gas contacting step is preferably performed by utilizing carbon monoxide in pure form or in admixture with inert gases. Preferably, the inert gas contacts the catalyst at the above-described temperatures in the absence of added gaseous oxygen except for gaseous oxygen which is present by virtue of its having been liberated from the solid during treatment. This particular requirement appears to be contrary to the teaching of certain patents (i.e. U.S. Pat. No. 3,915,892) in the area of catalyst manufacture of phosphorus-vanadium-oxygen catalysts for the production of maleic anhydride from lower aliphatics. This patent requires a controlled calcination procedure in which an oxygen-containing gaseous stream contacts the solid in the presence of a reducing gas. The purpose of this procedure is to selectively oxidize the catalyst under conditions in which vanadium is not oxidized so much as to reduce its catalytic effectiveness but requiring that oxygen contact the catalyst during a high temperature calcination in order for an effective catalyst to be prepared. The present claimed method requiring a reduction gas essentially free of added oxygen produces a good performing catalyst.

The contacting process can be performed at varying gas flow rates so that contact times and space velocities can vary. As long as a sufficient quantity of a reducing and/or inert gas reducing gas mixture is allowed to pass through and contact the catalyst source to prevent accumulation of any oxygen-containing gas which may be liberated from the catalyst, the reducing step contacting will be effective for the production of a good operating catalyst for the production of maleic anhydride from normal butane.

The total time of treatment or activation may vary anywhere from a few minutes to many hours, including from about 1 to about 48 hours at atmospheric pressure. It is anticipated that if the reduction contacting step takes place at elevated pressures that the time required for the activation and treatment to take place would be reduced accordingly.

The following examples are presented as specific embodiments of the present invention and are not necessarily presented to unduly limit or restrict the scope of the claims.

EXAMPLE I

A P-V-O-Zn catalyst-complex catalyst was prepared as generally described in U.S. Pat. No. 3,862,146, part B of Example I, by reacting vanadium pentoxide with concentrated hydrochloric acid under reflux with stirring for about one hour. Then zinc was added to the mixture and reacted for an additional period of time. 85 weight percent phosphoric acid was then added and the mixture was refluxed again until the reaction had been completed.

The solution was evaporated to a syrup in air at a temperature of from about 90° to 120° C. and thereafter raised to a temperature of from about 125° to 180° C to form a solid cake. The cake was ground to 20–30 mesh particle size combined with a Stereotex binder-lubricant and thereafter pelletized.

The pellets were then contacted under static air controlled conditions at a temperature of about 370° to 400° C to prevent a large exotherm from developing in the catalyst bed.

EXAMPLE II

About 30g of the dried catalyst from Example I was contacted at about 425° C in a stream of CO flowing at atmospheric pressure at a rate of 1.1 ft3/hr. for about 6 hours. The contacting took place in the absence of added gaseous oxygen.

EXAMPLE III

The catalysts prepared in Examples I and II above were tested under similar conditions for conversion of normal butane (1.1 percent in air at 1.43 hr$^{-1}$ WHSV based on the entire feed) to maleic anhydride. The results of this testing are reported in Table A where conversion is (lbs. butane reacted)/(lbs. of butane fed to the reactor), selectivity is (moles of maleic anhydride produced)/(moles of butane reacted) and weight yield is (lbs. maleic anhydride produced)/(lbs. of butane fed to the reactor). Using these definitions the theoretical weight yield for perfect conversion and selectivity is found to be 169 percent.

TABLE A

| CATALYST | REACTOR TEMP °C. | HOURS ON STREAM | % CONVERSION | % SELECTIVITY | % WEIGHT YIELD |
|---|---|---|---|---|---|
| EX. I (Non-treated) | 450 | 19 | 87 | 53 | 77 |
|  | 450 | 43 | 84 | 53 | 76 |
|  | 450 | 68 | 82 | 54 | 75 |
|  | 450 | 140 | 79 | 53 | 70 |
|  | 450 | 192 | 78 | 56 | 73 |
|  | 450 | 331 | 76 | 55 | 70 |
| EX. II (Treated) | 450 | 19 | 96 | 54 | 87 |
|  | 450 | 43 | 93 | 53 | 84 |
|  | 440 | 114 | 85 | 59 | 85 |
|  | 440 | 141 | 84 | 60 | 85 |
|  | 440 | 165 | 86 | 59 | 87 |
|  | 440 | 289 | 85 | 61 | 88 |
|  | 440 | 452 | 83 | 62 | 87 |

As indicated in the table above, carbon monoxide treatment enhanced the overall performance of the catalyst for conversion, selectivity and the ultimate weight yield of maleic anhydride.

EXAMPLE III

In this Example catalyst of Examples I and II above were tested for crush strength to determine the effects of carbon monoxide treatment. Each of the catalysts tested were essentially identical in pellet size (average particle length 4.8 mm). Twenty-eight individual crushing strength runs were made for each catalyst to allow a representative determination to be made.

The average crushing strength for the untreated catalyst (Example I) was found to be 11.4 lbs. while the values obtained for the carbon monoxide treated catalyst (Example II) were 17.2 lbs. indicating the enhanced strength attributed to the treated pellets.

EXAMPLE IV

The chloride content of the untreated catalyst of Example I was found to be about 0.5 weight percent. After this catalyst had been treated with carbon monoxide as in Example II it was found to contain 0.28 weight percent chloride. This is a favorable result as elimination of chlorides from the catalyst prior to its use in a commercial reactor eliminates a potential for corrosion to the plant especially if the treatment is performed during catalyst manufacture rather than in the plant reactor itself.

EXAMPLE V

Samples of catalyst prepared as detailed in Examples I and II above were analyzed by X-ray diffraction using a powder diffractometer having nickel filtered copper radiation. The $d$ spacing peaks and base line characteristics of the treated and untreated catalysts showed that there were internal crystalline changes that went beyond what would be normally expected from annealing of the catalyst from temperature treatments alone.

The changes in $d$ spacing values are shown below:

TABLE B

| Catalyst/d spacings | 3.90A | 3.30A | 3.14A |
|---|---|---|---|
| Example I | 46% | 100% | 96% |
| Example II | 71% | 76% | 100% |

We claim as our invention:

1. An improved phosphorus-vanadium-oxygen containing complex catalyst having an atomic ratio of phosphorus to vanadium in the range of from about 0.5–5 to 1 produced by a process comprising:

A. reacting a mixture comprising vanadium oxide, pentavalent phosphorus and hydrogen halide in an aqueous solution;
B. removing liquid from the mixture to form a solid; the improvement comprising:
  1. heating the solid to a temperature of less than about 470° C to effect liberation of water of hydration;
  2. contacting solid from step (1) with a reducing material comprising a gas selected from the group consisting of CO, $H_2$, and $H_2S$ and mixtures thereof at a temperature of from about 300° to about 600° C. and in the substantial absence of gaseous oxygen other than that liberated from the solid.

2. The composition of claim 1 further characterized in that said atomic ratio of phosphorus to vanadium is in the range of from about 1–2 to 1.

3. The composition of claim 2 further characterized in that said catalyst contains a metal activator selected from the group consisting of zinc, copper, lithium, bismuth or mixtures thereof in an atomic ratio of metal activator to vanadium in the range of from about 0.05–0.5 to 1.

4. The composition of claim 3 in that said activator is zinc and in an atomic ratio of zinc to vanadium in the range of from about 0.1–0.4 to 1.

5. The composition of claim 3 further characterized in that said activator is lithium.

6. The composition of claim 3 further characterized in that said activator is copper.

7. The composition of claim 3 further characterized in that said activator is bismuth.

8. The composition of claim 1 further characterized in that step (1) is performed while contacting the solid with an inert gas and in the absence of added molecular oxygen.

9. The composition of claim 8 further characterized in that the atomic ratio of phosphorus to vanadium is in the range of from about 1–2 to 1; said catalyst contains a zinc metal activator present in an atomic ratio of zinc to vanadium in the range of from about 0.05–0.5 to 1, said reducing gas comprises CO and the maximum temperature of step (2) is about 500° C.

10. The composition of claim 8 further characterized in that said inert gas is nitrogen.

11. In a method for production of a catalyst comprising a phosphorus-vanadium-oxygen complex having an atomic ratio of phosphorus to vanadium in the range of about 0.5–5 to 1 wherein said catalyst is produced by:
A. reacting a mixture comprising vanadium oxide compound, pentavalent phosphorus compound and hydrogen halide in an aqueous solution;
B. removing liquid from the mixture to form a solid; the improvement comprising:
  1. heating the solid to a temperature of less than about 470° C. to remove water of hydration;
  2. contacting solid from step (1) with a reducing material comprising a gas selected from the group consisting of CO, $H_2$ and $H_2S$ or mixtures thereof, at a temperature of from about 300° to 600° C and in the substantial absence of gaseous oxygen other than that liberated from the solid.

12. The method of claim 11 further characterized in that said atomic ratio of phosphorus to vanadium is in the range of from about 1–2 to 1.

13. The method of claim 12 further characterized in that said catalyst contains a metal activator selected from the group consisting of zinc, copper, lithium, bismuth or mixtures thereof in an atomic ratio of metal activator to vanadium in the range of from about 0.05–0.5 to 1.

14. The method of claim 13 in that said activator is zinc and in an atomic ratio of zinc to vanadium is in the range of from about 0.1–0.4 to 1.

15. The method of claim 13 further characterized in that said activator is lithium.

16. The method of claim 13 further characterized in that said activator is copper.

17. The method of claim 13 further characterized in that said activator is bismuth.

18. The method of claim 11 further characterized in that step (1) is performed while contacting the solid with an inert gas and in the absence of added molecular oxygen.

19. The method of claim 18 further characterized in that the atomic ratio of phosphorus to vanadium is in the range of from about 1–2 to 1; said catalyst contains a zinc metal activator present in an atomic ratio of zinc to vanadium in the range of from about 0.05–0.5 to 1, said reducing gas comprises CO and the maximum temperature of step (2) is about 500° C.

20. The method of claim 18 further characterized in that the inert gas is nitrogen.

* * * * *